United States Patent [19]
DiNapoli

[11] Patent Number: 5,984,855
[45] Date of Patent: Nov. 16, 1999

[54] MAGNETIC BLANKET FOR HORSES

[75] Inventor: Lisanne DiNapoli, Riviera Beach, Fla.

[73] Assignee: Magnetherapy, Inc.

[21] Appl. No.: 09/078,526

[22] Filed: May 13, 1998

[51] Int. Cl.[6] .............................. B68C 5/00; A01K 13/00
[52] U.S. Cl. .............................................................. 600/15
[58] Field of Search .............................. 600/9–15; 54/79, 54/166, 79.4, 82; 224/905; 119/850

[56] References Cited

U.S. PATENT DOCUMENTS

| | | | |
|---|---|---|---|
| 5,177,940 | 1/1993 | Paul | 54/79 |
| 5,271,211 | 12/1993 | Newman | 54/79.2 |
| 5,426,925 | 6/1995 | Smargiassi | 600/15 X |

OTHER PUBLICATIONS

William Philpott, "Biomagnetic Handbook Today's Introduction to The Energy Medicine of Tomorrow", p. 21, Dec. 1990.

*Primary Examiner*—Samuel Gilbert
*Attorney, Agent, or Firm*—McHale & Slavin PA

[57] ABSTRACT

The instant invention is a magnetic blanket for equine therapy. The blanket takes advantage of "unipolar" ceramic magnets and is useful for treating certain horse ailments and for enhanced warm-up and cool-down of the horse. The ceramic magnets are strategically positioned so as to provide an effective means for reducing pain and inflammation and stimulating soft tissue healing in horses.

5 Claims, 2 Drawing Sheets

MAGNETIC BLANKET FOR HORSES

FIELD OF THE INVENTION

This invention relates to the field of magnetic therapy and particularly relates to the use of unidirectional "unipolar" ceramic magnets in a blanket for reducing pain and inflammation and stimulating soft tissue healing in horses.

BACKGROUND OF THE INVENTION

In recent years numerous studies have demonstrated that permanent magnetic fields can have a profound effect on a number of biological processes. Most recently it has been recognized that magnetic field energy can modify many physiological processes ranging from cellular and membrane functioning to alterations in the mechanical properties of important tissues and organs. The use of permanent magnets and electromagnetic fields for the treatment of musculoskeletal injuries and pathologies have opened new avenues in both human and veterinary medicine.

Permanent magnets provide a practical non-invasive method for stimulation of cells and tissues. This stimulation results in an acceleration of the healing process which is believed to result from enhanced tissue repair and regeneration.

In equine therapy, magnetic and electromagnetic fields can be used for the treatment of various musculoskeletal injuries and pathologies which may occur in horses during their daily routines and participation in various competitions. The most effective applications of permanent magnets are related to bone unification, wound healing and the reduction of pain and inflammation.

Attempts have been made to provide magnetic or magnetizable coverings as a means of treating various ailments. For instance, U.S. Pat. No. 5,426,925 issued to Smargiassi claims a horse blanket having rows of laterally positioned magnets each in the range of 500–120 gauss. The patent uses lateral rows of magnets that are sewn in, pocketed, or heat sealed within a pocket.

U.S. Pat. No. 4,587,956 issued to Griffin discloses a reversible magnetic therapeutic device containing a plurality of magnets spaced apart across its length and width so as to provide a two-dimensional array with all the North poles and South poles on opposite sides. Magnetic flux concentrations in the range of about 200 to 6400 gauss per square inch are utilized.

U.S. Pat. No. 4,489,711 to Latzke discloses a magnetic plaster which may be utilized for therapeutic purposes. The plaster consists of a flexible sheet which may be adhered to a patient which contains magnetizable particles of ferrite or chromium dioxide therein. Latzke discloses that while it is possible to form unipolar sheets wherein only a Northern or Southern pole faces the skin surface, the use of alternately arranged positive arid negative poles are preferred. Latzke utilizes a magnetized sheet having a flux density in the range of 50–2000 gauss.

The problem with the known prior art devices and related horse blankets is their use of bipolar magnets which contain both positive and negative magnetic polarity on the same side, thereby making them less effective. Additionally, the prior art horse blankets were made of materials which held moisture close to the horse's body resulting in chafing and increased drying time. Lastly, none of the prior art horse blankets recognized the need for determining strategic locations for the placement of concentrated bands of magnetic material such that the maximum therapeutic effect could be realized.

Thus, what is lacking in the art is a magnetic blanket for equine therapy capable of delivering a magnetic field to targeted tissues whereby stronger and deeper penetration is accomplished, to provide an improved magnetic blanket useful as an aid to warm-up preparation before riding to enhance blood circulation and oxygen delivery and after competition to prevent soreness and stiffness, and to provide an increased wicking of moisture away from the horse's body while simultaneously exhibiting a much faster drying rate than prior art blankets.

SUMMARY OF THE INVENTION

The invention is directed toward a magnetic blanket for equine therapy. The blanket takes advantage of "unipolar" technology, utilizing TECTONIC® unidirectional "unipolar" ceramic magnets. All unidirectional "unipolar" magnets are placed with their negative poles towards the body. The use of this unidirectional "unipolar" technology in combination with the instant invention's unique strategic bilateral placement of bands of magnets, has been demonstrated as giving superior penetration when compared to bipolar technology. Most competitive magnetic blankets have both positive and negative magnetic poles on the same side which renders them less effective in providing the deep tissue penetration necessary for improved healing.

The TECTONIC® unidirectional "unipolar" ceramic magnets of the present invention have a higher gauss rating than the magnets normally used in most competitive products. The magnets of the instant invention have a gauss rating in the range of 1200 to 3950 gauss. In comparison to prior art magnets, the magnets of the instant invention provide a higher level of generated magnetic field thereby providing up to an order of magnitude greater penetration of the strategically targeted areas.

The improved magnetic blanket of the instant invention is formed utilizing a tetra-channel polyester fiber marketed under the brand name COOLMAX® CORDURA from the DuPont company. The COOLMAX® material quickly wicks moisture away from the horse's body while having a drying rate three times faster than cotton. The blanket thereby maintains a dry and comfortable environment for the horse. Lastly, the soft, durable COOLMAX® fabric is non-chafing, washable and dryable and is resistant to mildew and shrinkage.

It is therefore an objective of the present invention to provide an improved magnetic blanket for equine therapy.

It is a further objective of the invention to provide a magnetic blanket capable of delivering a significantly stronger magnetic field to the targeted tissues whereby stronger and deeper penetration is accomplished.

It is a still further objective of the present invention to provide an improved magnetic blanket useful as an aid to warm-up preparation before riding to enhance blood circulation and oxygen delivery and after competition to prevent soreness and stiffness.

It is yet another objective of the present invention to provide an improved magnetic blanket capable of providing increased wicking of moisture away from the horse's body while simultaneously exhibiting a much faster drying rate than prior art blankets.

Other objectives and advantages of the present invention will become apparent to those skilled in the art from the following detailed description when read in conjunction with the accompanying drawings.

DETAILED DESCRIPTION OF THE INVENTION

Figure 1:
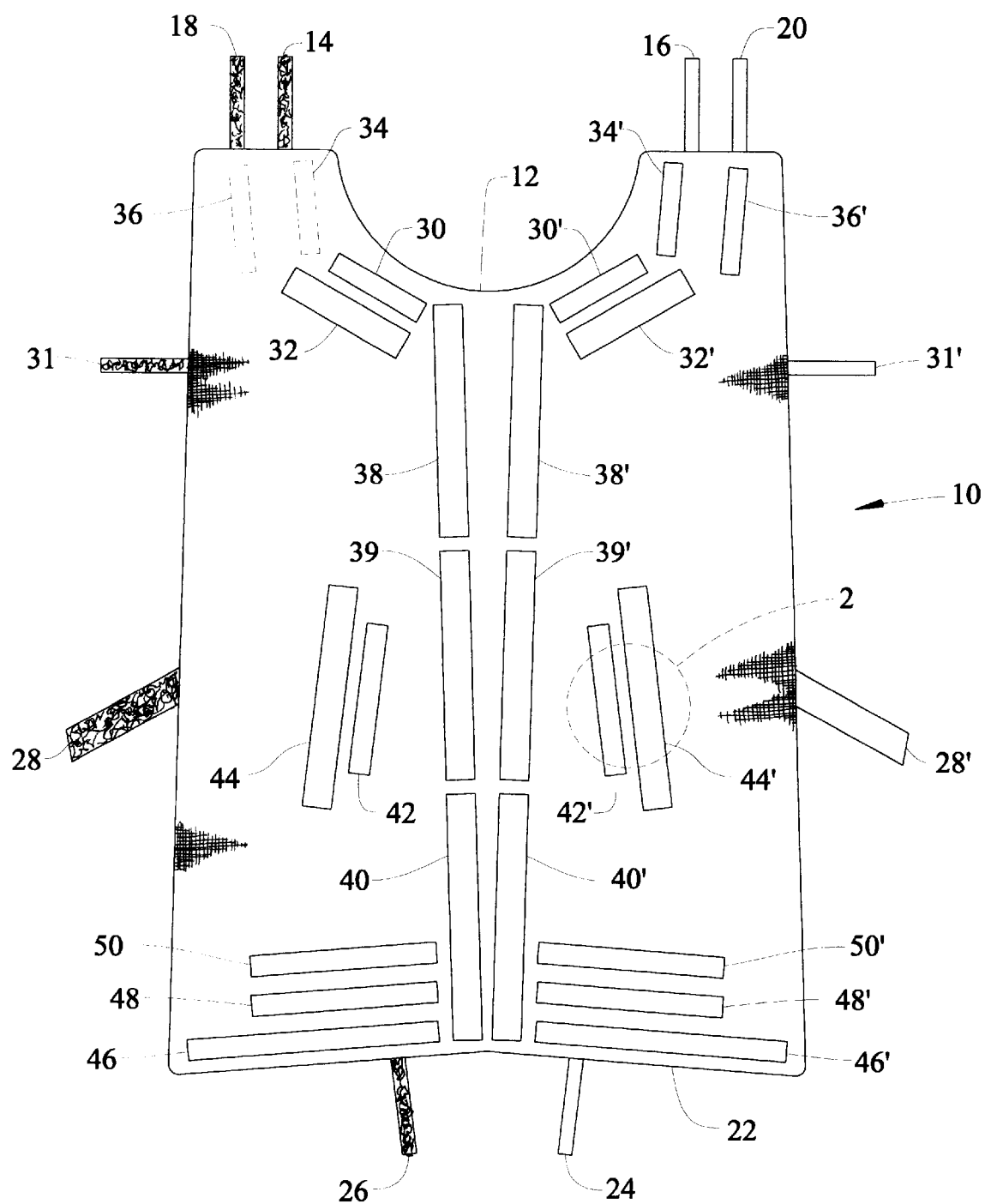
FIG. 1 is a bottom plan view of the improved horse blanket.

With reference to FIG. 1, the magnetic blanket 10 of the instant invention is preferably constructed from a wicking material such as DuPont COOLMAX® CORDURA fabric and is shaped to conform to a horse's body for a proper fit. The front end 12 of the blanket which closes around the horse's neck and chest area, is made adjustable by several sets of closure straps. Straps 34,34' and 36,36' include hook and pile type fasteners for ease of application and adjustment. A second set of closure straps 14,16 and 18,20 also include adjustable buckles and clips for ease of application and allow for a secure fit around the neck area of the horse. It should be noted that various types of fasteners such as hook and pile ("VELCRO"), snaps, buckles, clips and the like each provide suitable closure and the changing thereof does not defeat the scope of this invention.

The back end 22 of the blanket 10 includes an adjustable tail straps 24 and 26 which can be placed either above or below the tail of the horse. Two reinforced surcingles 28,28' and 31,31' complete the securement of the blanket 10 to the horse's coat and are useful for maintaining the proximity of the blanket while in use.

The magnetic blanket 10 includes twenty flexible magnetic bands contained in a wick material such as that used in the construction of the blanket. Each band is backed with hook and pile type fastener material and designed so as to mate with hook and pile type fastener material attached to strategically chosen locations on the blanket as depicted in the figure. In particular, neck bands 30 and 30' each contain 13–15 magnets and are juxtapositioned to the neck area as defined by the front end 12. Neck bands 32 and 32' are placed adjacent to the neck bands 30, 30' and each contain 13–15 magnets.

Vertebrae bands 38,38', 39,39' and 40,40' each contain 13–15 magnets and are strategically positioned along the spinal area between the withers and the dock of the horse for treating the spinal area including the vertebrae and ribs of the horse. Short rib cage bands 42 and 42' each contain 5 magnets with long rib cage band 44 and 44' which each contain 9 magnets placed at an angular slope so as to cover the outermost area of the rib cage. These four strips are positioned to the front of the hindquarter below the spine where the abdominal oblique muscles are attahced to the rib cage.

Bands 46 and 46' each containing 18–20 magnets are further arranged so as to provide for strategic treatment of the rear of each hindquarter. They treat the semitendinosus, coccygeus and gluteal muscles and cover the stifle and pelvic areas. The bands are placed adjacent to the back end 22 with additional bands 48, 48' and 50, 50' each having 13–15 magnets to concentrate treatment on the area having the most powerful muscles. They effect a majority of the hindquarter. Most of the gluteal and biceps femoris are in this area.

The arrangement of the magnets in bands with the use of hook and pile type fastener material allows for easy detachment of the magnets for laundering of the blanket or when it is desirable to only treat a specific portion of the horse's anatomy with therapeutic magnetic energy. The bands are designed so as to encase a plurality of the unidirectional magnets of the invention, in a unipolar alignment, and spaced so as to maintain the desired therapeutic magnetic effect when attached to the strategically chosen points previously defined on the blanket.

Figure 2:
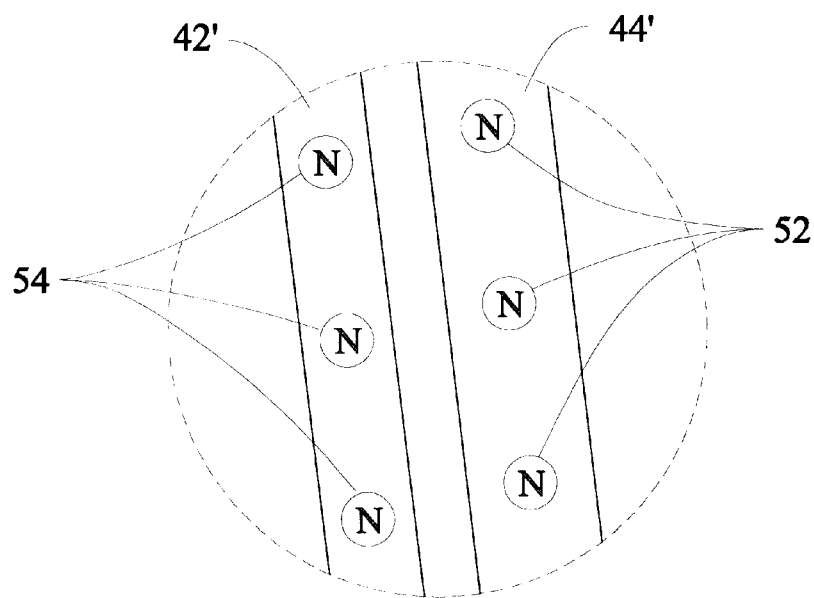
FIG. 2 is a partial cut-away view of area

Now referring to FIG. 2, band 44' is shown encasing the TECTONIC® ceramic unidirectional "unipolar" high gauss magnets 52 which are arranged so that the negative poles are all facing toward the animal. Band 42' is also shown encasing TECTONIC® ceramic magnets 54 which are arranged so that the negative poles are all facing toward the animal. It should be noted that while TECTONIC® ceramic magnets are cited, any type of high quality magnet having a gauss rating in the range of 1200 to 3950 and being a ceramic unidirectional "unipolar" disc will suffice.

The magnets are spaced apart approximately 15 mm and are glued in pre-cut holesw in foam and covered by the COOLMAX® CORDURA fabric. The hook and pile type fastener strip is then glued and sewn to the outside (positive pole side) of the strip. All the strips have a 1" tab at each end to facilitate removal from the blanket. The bands can be washed independently of the blanket or replaced by higher/lower gauss ratings or by higher/lower amounts of magnets. This allows the blanket to be customized to treat a particular horse ailment. The preferred arrangement results in the utilization of a total of 276 magnets.

Figure 3:
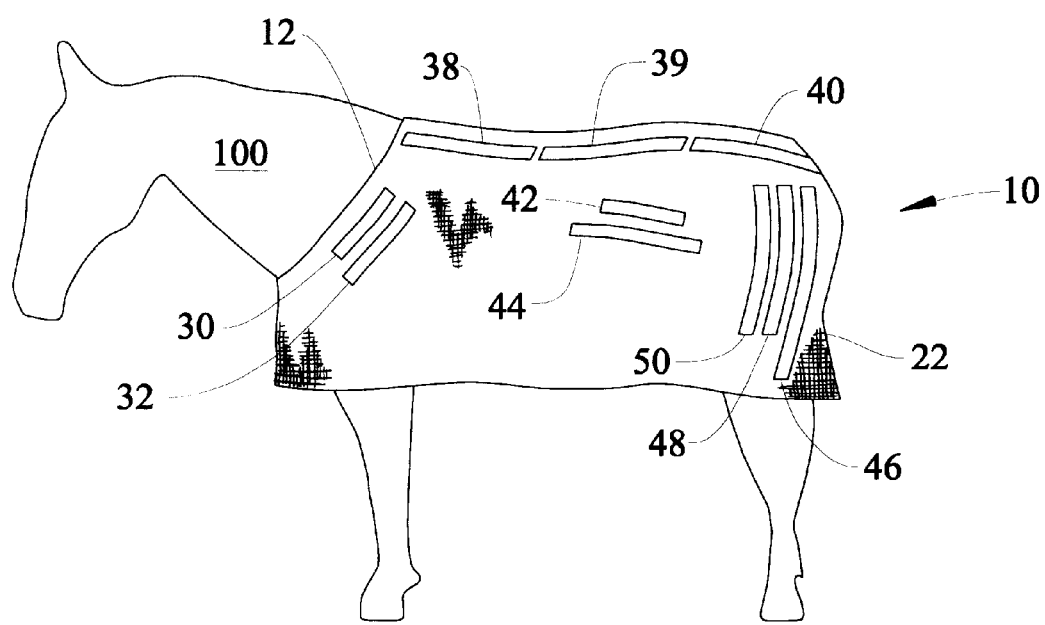
FIG. 3 is a pictorial view of the improved horse blanket as applied to a horse.

With reference to FIG. 3, the blanket is shown as it is placed on a horse 100. Only one side of the horse is shown for illustration, however the viewer should be cognizant that there are equivalent magnetic bands placed in symmetrical positions on the opposite side of the horse. The placement of each magnetic band at a strategic area, as shown by the shaded bands, enables the blanket to provide strong and soothing magnetic therapy of the major joints and muscle groups. The magnetic therapy delivered by the blankets is effective in treating soreness and stiffness along the spinal column and the associated muscles including the shoulders, vertebrae, ribs, stifles, hips and pelvis.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

I claim:

1. A unipolar ceramic magnetic blanket adapted to conform to the shape of a horse's body comprising:

a blanket formed from a tetra-channel polyester fiber constructed and arranged so as to wick moisture from the horse's body, including one portion of a hook and pile fastening material;

a plurality of unidirectional ceramic magnets having a gauss rating within the range of 1200–3950 and being strategically located so as to deliver a therapeutic magnetic benefit to said horse, wherein said magnets are provided in a plurality of flexible bands arranged so that their negative poles face the horse's body, and having a corresponding portion of the hook and pile fastening material attached thereto;

and a means for securing said blanket to said horse;

whereby non-invasive, safe and effective therapy is accomplished resulting in markedly improved performance and reduced soreness and stiffness after competition.

2. The blanket according to claim 1 wherein about twenty flexible magnetic bands are bilaterally placed at strategic locations so as to provide effective magnetic therapeutic treatment to the spinal column, vertebra, shoulders, hips, stifles and pelvic areas and which result in the application of about 276 magnets.

3. A unipolar ceramic magnetic blanket adapted to conform to the shape of a horse's body comprising:

a blanket formed from a tetra-channel polyester fiber constructed and arranged so as to wick moisture from the horse's body, including one portion of a hook and pile fastening material;

a plurality of unidirectional ceramic magnets having a gauss rating within the range of 1200–3950 and being strategically and removably located so as to deliver a therapeutic magnetic benefit to the spinal column and associated muscles of said horse while allowing for ease of maintenance;

wherein said magnets are provided in a plurality of flexible bands, each band containing an effective amount of ceramic unidirectional magnets arranged so that their negative poles face the horse's body, and having a corresponding portion of the hook and pile fastening material attached thereto, whereby each magnetic band may be strategically placed in an area to cover the major joint and muscle groups;

said blanket having an adjustable closure which closes around the neck and chest areas including a plurality of hook and pile type fasteners constructed and arranged so as to enable said blanket to conform to the horse's body thereby providing a proper fit; and an adjustable tail strap and surcingles;

whereby non-invasive, safe and effective therapy is accomplished resulting in markedly improved performance and reduced soreness and stiffness after competition.

4. The blanket according to claim 3 wherein 20 flexible magnetic bands are bilaterally placed at strategic locations so as to provide effective magnetic therapeutic treatment to the spinal column, vertebra, shoulders, hips, stifles and pelvic areas and which result in the application of a total of 276 magnets.

5. The blanket according to claim 3 wherein from 5 to 18 magnets are included per band dependent upon the length of the band.

* * * * *